(12) United States Patent
Danielmeier et al.

(10) Patent No.: US 7,307,140 B2
(45) Date of Patent: Dec. 11, 2007

(54) POLYASPARTIMIDES

(75) Inventors: Karsten Danielmeier, Solingen-burg (DE); Charles A. Gambino, McDonald, PA (US); Rolf Gertzmann, Leverkusen (DE); Richard R. Roesler, Wexford, PA (US); Terrell D. Wayt, Moundsville, WV (US); Edward P. Squiller, Bridgeville, PA (US); Michele E. Honko, Pittsburgh, PA (US); Karen Marie Henderson, Coraopolis, PA (US)

(73) Assignee: Bayer MaterialScience LLC, Pittsburgh, PA (US)

( * ) Notice: Subject to any disclaimer, the term of this patent is extended or adjusted under 35 U.S.C. 154(b) by 361 days.

(21) Appl. No.: 10/990,082

(22) Filed: Nov. 16, 2004

(65) Prior Publication Data

US 2006/0106194 A1    May 18, 2006

(51) Int. Cl.
*C08F 73/10* (2006.01)
*C08F 283/04* (2006.01)

(52) U.S. Cl. ............... 528/310; 528/322; 528/328; 525/420; 525/421; 525/422; 525/424; 525/540

(58) Field of Classification Search ............... 528/310, 528/322, 328; 525/420, 421, 422, 424, 540
See application file for complete search history.

(56) References Cited

U.S. PATENT DOCUMENTS

| | | | |
|---|---|---|---|
| 5,126,170 A | 6/1992 | Zwiener et al. | 427/385.5 |
| 5,214,086 A | 5/1993 | Mormile et al. | 524/237 |
| 5,236,741 A | 8/1993 | Zwiener et al. | 427/385.5 |
| 5,243,012 A | 9/1993 | Wicks et al. | 528/58 |
| 5,364,955 A | 11/1994 | Zwiener et al. | 556/418 |
| 5,412,056 A | 5/1995 | Zwiener et al. | 528/73 |
| 5,489,704 A | 2/1996 | Squiller et al. | 560/35 |
| 5,559,204 A | 9/1996 | Squiller et al. | 528/84 |
| 5,623,045 A | 4/1997 | Zwiener et al. | 528/68 |
| 5,736,604 A | 4/1998 | Luthra | 524/591 |
| 5,821,326 A | 10/1998 | Kurek et al. | 528/332 |
| 5,847,195 A | 12/1998 | Roesler | 560/35 |
| 6,005,062 A | 12/1999 | Hansen et al. | 528/68 |
| 6,183,870 B1 | 2/2001 | Hergenrother et al. | 428/423.1 |
| 6,355,829 B2 | 3/2002 | Roesler et al. | 560/25 |
| 6,458,293 B1 | 10/2002 | Roesler et al. | 252/182.23 |
| 6,482,333 B1 | 11/2002 | Roesler et al. | 525/182.12 |
| 6,911,501 B1 * | 6/2005 | Danielmeier et al. | 525/422 |

FOREIGN PATENT DOCUMENTS

| | | |
|---|---|---|
| EP | 667 362 A1 | 8/1995 |
| WO | 2005/073188 A1 | 8/2005 |

OTHER PUBLICATIONS

Verhey H J et al: "Crosslinking and drying of a two-component waterborne coating monitored by a functionalized charge-transfer fluorescence probe" Polymer, Elsevier Science Publishers B.V, GB, vol. 38, No. 17, Aug. 1997, pp. 4491-4497, XP004083104.

Andersson, Lars et al: Poly(ethylene glycol)-poly(ester-carbonate) block copolymers carrying PEG-peptidyl-doxorubicin pendant side chains: synthesis and evaluation as anticancer conjugates Biomacromolecules, 6(2), 914-926 Coden: Bomaf6; ISSN: 1525-7797, 2005, XP002401856.

* cited by examiner

*Primary Examiner*—Duc Truong
(74) *Attorney, Agent, or Firm*—Noland J. Cheung; Robert S. Klemz

(57) ABSTRACT

The present invention relates to novel polyaspartimides, their method of production and the use of these polyaspartimides as reactive components for polyisocyanates in two-component polyurethane coating compositions. The polyaspartimides are prepared by reacting a polyether amine with a maleimide.

5 Claims, No Drawings

POLYASPARTIMIDES

BACKGROUND OF THE INVENTION

The present invention relates to novel polyaspartimides, a process for preparing them from specific primary amines and maleimides and to their use as reactive components for polyisocyanates in two-component polyurethane coating compositions.

Two-component coating compositions which contain, as binder, a polyisocyanate component combined with one or more isocyanate-reactive components are known. They are suitable for preparing high quality coatings which are hard, elastic, abrasion resistant, solvent resistant and weather resistant.

Secondary polyamines which contain ester groups have become established in the two-component surface coating industry. They are particularly suitable, in combination with lacquer polyisocyanates, as binders in low-solvent or solvent-free, high solids coating compositions because they provide rapid curing of the coatings at low temperatures.

These secondary polyamines are polyaspartates and are described, e.g., in U.S. Pat. Nos. 5,126,170, 5,214,086, 5,236,741, 5,243,012, 5,364,955, 5,412,056, 5,623,045, 5,736,604, 6,183,870, 6,355,829, 6,458,293 and 6,482,333 and published European Patent Application 667,362. In addition, aspartates containing aldimine groups are also known (see U.S. Pat. Nos. 5,489,704, 5,559,204 and 5,847,195). Secondary aspartic acid amide esters are also known (see U.S. Pat. No. 6,005,062). Their use as the only isocyanate-reactive component or mixed with other isocyanate-reactive components in two-component coating compositions are also described in the above-identified patents. The process for preparing these polyaspartates is the reaction of the corresponding primary polyamines with maleates or fumarates resulting in the formation of secondary polyamines. Due to steric, structural and electronic effects, these secondary amino groups have sufficiently reduced reactivity towards isocyanate groups to be mixable with polyisocyanates in a reliable and easy manner.

As is known in the art, the reaction which is used to prepare polyaspartates is the addition of primary amines to the activated C-C double bond in vinyl carbonyl compounds. It has been found, however, that this reaction does not proceed to completion during the course of the actual synthesis process (e.g., 24 hours with stirring at 60° C.). The actual extent of the reaction is dependent upon the type of primary polyamine. Thus, the degree of conversion (measured by the concentration of free, unconverted maleate and fumarate, into which maleate rearranges in the presence of basic catalysts) after 1 day with 1,6-hexanediamine is about 90 to 93%. The degree of conversion after 1 day with a cycloaliphatic polyamine having sterically hindered primary amino groups, i.e., 4,4'-diamino-3,3'-dimethyidicyclohexyl-methane is only 77%. Complete or essentially complete conversion is achieved only after several days or, in the case of 4,4'-diamino-3,3'-dimethyidicyclohexyl-methane, only after several months.

In a typical commecial production, the reaction is run for sixteen hours when the conversion is somewhere between 75 and 95% complete depending on the amine used. The "unfinished" material is drummed and held in storage until the reaction is complete. This typically takes anywhere from two weeks to six months. U.S. Pat. No. 5,821,326 describes the use of certain five-membered aromatic ring compounds as catalyst to accelerate the preparation of the aspartates.

The conventional aspartates are capable of a further transformation (after curing with an isocyanate) to form a hydantoin ring structure. This hydantoin formation might lead to a shrinking of the coating and undesired alcohol formation. It would also be desirable to prepare an aspartate that would be less prone to hydantoin formation.

U.S. application Ser. No. 10/761,643, filed on Jan. 21, 2004, describes the preparation of aspartates by reacting an excess of primary amine with a maleate or fumarate and then reacting the resultant product with a maleimide to form a product which has both aspartate groups and aspartimide groups.

DESCRIPTION OF THE INVENTION

The present invention is directed to novel polyaspartimides of the formula:

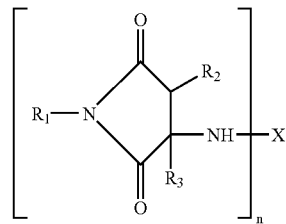

where
X represents an n-valent polyether radical obtained by the removal of n amino groups from a polyether amine corresponding to the formula, $X—(NH_2)_n$, wherein said polyether amine has a number average molecular weight of from about 200 to about 6000, and may contain further functional groups that either are reactive with isocyanate groups or are inert to isocyanate groups at temperatures of up to 100° C.,
$R_2$ and $R_3$ may be the same or different and represent moieties selected from the group consisting of i) hydrogen, ii) straight or branched $C_1$ to $C_8$ alkyl groups, which may be substituted with up to three aryl groups containing from 6 to 10 carbon atoms, iii) $C_6$ to $C_{10}$ aryl groups, which may be substituted with up to three alkyl groups having from 1 to 3 carbon atoms, and iv) together form a five or six-membered cycloalkyl group, with said cycloalkyl group being substituted with from 0 to 3 alkyl groups having from 1 to 3 carbon atoms,
$R_1$ represents a moiety selected from the group consisting of i) hydrogen, ii) straight or branched $C_1$ to $C_8$ alkyl groups, which may be substituted with up to three aryl groups containing from 6 to 10 carbon atoms, and iii) $C_6$ to $C_{10}$ aryl groups, which may be substituted with up to three alkyl groups having from 1 to 3 carbon atoms, and
n represents an integer of from 2 to 4.

The products of the present invention, when combined with a polyisocyanate, have longer potlifes and provide for harder coatings than polyether-based aspartates of the prior art. In addition, the products have less of a tendency to form hydantoin rings.

The present invention also relates to a process for preparing polyaspartimides of the above formula comprising reacting at a temperature of from about room temperature to about 100° C., in solution or in the absence of a solvent, di- or polyamines corresponding to formula $$X[—NH_2]_n$$

with a maleimide, in a maleimide to amine group equivalent ratio of from about 0.95:1 to about 1.05:1 and wherein X and n are as defined above. The most preferred ratio is 1:1.

The present invention also relates to a two-component coating composition which contains, as binder,
a) a polyisocyanate component and
b) an isocyanate-reactive component containing
b1) a compound corresponding to the polyaspartimde of the invention and
b2) optionally other isocyanate-reactive compounds, wherein the equivalent ratio of isocyanate groups to isocyanate-reactive groups is from about 0.8:1 to about 2:1, and optionally, additives known in surface coatings technology.

The molecular weights are number average molecular weights ($M_n$) and are determined by end group analysis (NH number).

Suitable polyamines correspond to the polyether polyols known and used in the art, e.g., to prepare isocyanate terminated prepolymers with the exception that the terminal hydroxy groups are converted to amino groups, either by amination or by reacting the hydroxy groups with a diisocyanate and subsequently hydrolyzing the terminal isocyanate group to an amino group. Preferred polyamines are amine-terminated polyethers such as the Jeffamine resins available from Huntsman.

The polyether amine component includes any polyether amine that can accomplish the objects of the invention. Suitable polyether amines generally include difunctional and multi-functional amines with polypropylene oxide groups. These amines are well known and can be prepared by methods such as those described in German Offenlegungsschrift 1,193,671, U.S. Pat. No. 3,236,895 and French Patent. No.1,466,708, the disclosures of which are herein incorporated reference. Suitable examples of difunctional amines are polypropylene oxide diamines available from Huntsman Corporation, such as Jeffamine D-230, JeffamineD-400 and Jeffamine D-2000. Examples of suitable trifunctional polypropylene oxide amines include polyoxypropylene triamine, (Jeffamine T-403), Jeffamine T-3000 and Jeffamine T-5000, also available from Huntsman. It is believed that multifunctional polyether amines, e.g., tetrafunctional polypropylene oxide amines, can also be used.

Useful maleimides are those of the structure:

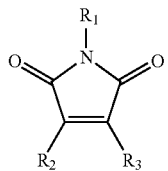

where $R_1$, $R_2$, and $R_3$ are as defined above. Specifically useful maleimides include N-methyl maleimide, N-ethyl maleimide, N-propyl maleimide, N-isopropyl maleimide, N-isobutyl maleimide, N-butyl maleimide, N-amyl maleimide, N-ethylamyl maleimide, N-methylisoamyl maleimide, N-methylhexyl maleimide, N-phenyl maleimide, N-ethyl-2-methylmaleimide, N-2,3-trimethyl maleimide, 3-methyl-N-phenyl maleimide, N-phenyl-3,4,5,6-tetrahydrophthalimide and 3-phenyl-N-phenyl maleimide.

The reaction is typically conducted at a temperature of from about 50 to about 100° C., for times ranging from about 1 to about 4 hours. The maleimide to amine group equivalent ratio is from about 0.95:1 to about 1.05:1, with a 1:1 ratio being particularly preferred. Any excess maleimide can then be removed to give a 100% resinous product, or it can remain and can serve as a plasticizer. If an excess of amine is used, it can generally be tolerated, but such a product will have a higher reactivity and will shorten the pot life of the overall system.

The process to prepare the polyaspartimides of the present invention may either be performed in solution or in the absence of a solvent. Solvent may also be added after the synthesis process, for example, to lower the viscosity. Suitable solvents include any organic solvents, preferably those known from surface coating technology which do not react with either reaction partner. Examples include n-butyl acetate, methoxy-propyl acetate, toluene, xylene and higher aromatic solvents (such as the Solvesso solvents from Exxon).

The polyaspartimides prepared according to the invention may be directly used as reactive components for polyisocyanates after concluding the synthesis process.

One use of the polyaspartimides of the present invention is to prepare coatings from two-component coating compositions containing, as binder,
a) a polyisocyanate component and
b) an isocyanate-reactive component containing
b1) one or more polyaspartimide of the invention and
b2) optionally other known isocyanate-reactive components.

Suitable polyisocyanate components a) are known and include the polyisocyanates known from polyurethane chemistry, e.g., low molecular weight polyisocyanates and lacquer polyisocyanates prepared from these low molecular weight polyisocyanates. Preferred are the lacquer polyisocyanates, which are known from surface coating technology. These lacquer polyisocyanates can contain biuret groups, isocyanurate groups, allophanate groups, uretdione groups, carbodiimide groups and/or urethane groups and are preferably prepared from (cyclo)aliphatic polyisocyanates.

Suitable low molecular weight polyisocyanates for use in accordance with the present invention or for preparing the lacquer polyisocyanates are those having a molecular weight of 140 to 300, such as 1,4-tetramethylene diisocyanate, 1,6-hexamethylene diisocyanate (HDI), 2,2,4- and/or 2,4,4-trimethyl-hexamethylene diisocyanate, dodecamethylene diisocyanate, 2-methyl-1,5-diisocyanatopentane, 1,4-diisocyanatocyclohexane, 1-isocyanato-3,3,5-trimethyl-5-isocyanato-methylcyclohexane (IPDI), 2,4- and/or 4,4' diisocyanato-dicyclohexyl-methane, 1-isocyanato-1-methyl-3(4)-isocyanatomethyl-cyclohexane (IMCI), 2,4- and/or 2,6-hexahydrotoluylene diisocyanate ($H_6TDI$), 2,4- and/or 4,4'-diisocyanatodiphenylmethane or mixtures of these isomers with their higher homologs (which may be obtained in known manner by the phosgenation of aniline/formaldehyde condensates), 2,4- and/or 2,6-diisocyanatotoluene, and mixtures thereof. The use of low molecular weight polyisocyanates themselves is not preferred. Also, lacquer polyisocyanates prepared from aromatic polyisocyanates, such as 2,4- and/or 2,6-diisocyanatotoluene, are also less preferred. The lacquer polyisocyanates containing urethane groups are preferably based on low molecular weight polyhydroxyl compounds having molecular weights of 62 to 300, such as ethylene glycol, propylene glycol and/or trimethylol-propane.

Preferred lacquer polyisocyanates for use as component a) are those based on 1,6-hexamethylene diisocyanate and having an NCO content of 16 to 24 wt. % and a maximum viscosity at 23° C. of 10,000, preferably 3,000 mPa·s. Preferred also are those isocyanates based on TPDI.

Optional starting components b2) are known compounds containing at least two isocyanate-reactive groups, including groups which react with isocyanate groups under the effect of either moisture or/and heat. Examples include hydroxy-functional polyacrylates, polyesterpolyols, and polyether polyols and aspartates and aldimines of the type known in the art. Mixtures of such compounds may also be used.

In the binders used according to the invention, the amounts of components a), b1) and (optionally) b2) are selected such that the equivalent ratio isocyanate groups to isocyanate-reactive groups is from about 0.8:1 to about 2.0:1, and preferably from about 0.8:1 to about 1.2:1.

The binders according to the invention are prepared by mixing the individual components either in the absence of a solvent or in the presence of the solvents which are conventionally used in polyurethane surface coating technology. Suitable solvents include ethyl acetate, butyl acetate, methoxypropyl acetate, methyl isobutyl ketone, methyl ethyl ketone, xylene, N-methylpyrrolidone, petroleum spirit, chlorobenzene, Solvesso solvent or mixtures thereof.

Preferably, the ratio by weight of binder components a) and b) to solvent in the coating compositions according to the invention is from about 40:60 to about 100:0, more preferably from about 60:40 to about 100:0.

The coating compositions may also contain the known additives from surface coating technology. These include pigments, fillers, flow control agents, catalysts and anti-settling agents.

The properties of the coatings obtained from the coating compositions according to the invention may be adjusted by appropriate selection of the type and ratios of starting components a), b1) and b2).

The coating compositions may be applied to any substrate in a single layer or in several layers by known methods, e.g., by spraying, painting, immersing, flooding or by using rollers or spreaders. The coating compositions according to the invention are suitable for preparing coatings on substrates, such as metals, plastics, wood or glass. The coating compositions are especially suitable for coating steel sheeting, which is used for the production of vehicle bodies, machines, cladding panels, barrels and containers. The substrates may be provided with suitable primer coats prior to applying the coating compositions according to the invention. Drying of the coatings may take place at a temperature of about 0 to 160° C.

The polyaspartimides of the present invention may be directly used after completion of the synthesis process because, in contrast to prior art aspartates, an approximately complete degree of conversion is achieved. The products exhibit a reasonable, as opposed to a vigorous, reactivity towards isocyanates. Due to their low viscosity, they are a more than suitable alternative, as reactive diluents, to the environmentally polluting organic solvents previously used and may therefore be used in high quality, low-solvent or even solvent-free, high solids, two-component coating compositions.

The maleimide reacts much faster than dialkyl maleate because the cis-trans isomerization, which can occur when the maleate ester isomerizes to fumarate and slows the reactivity, is not possible in the maleimide. This is an advantage because of the reduction of the synthesis time and the elimination of the aging process. Another advantage is that the succinimide moiety is not capable of a further transformation (after curing with an isocyanate) to form a hydantoin ring structure as do aspartate esters. This hydantoin formation is accompanied by alcohol elimination and that might lead to shrinkage in the coating. Yet another advantage of this technology is the possibility to form aspartimides based on slow amines like Jeffamine polyamines. Surprisingly the product based on Jeffamine polyamines and maleimide can be completely formed in a short time compared to the reaction of Jeffamine polyamines with diethylmaleate. Reaction of maleimide with Jeffamine polyamine is complete in a matter of hours compared to that of diethyl maleate with a Jeffamine, which are so slow that the Jeffamine is only 50% converted to the aspartate in six months. This offers the possibility to synthesize aspartate-type coreactants with much more flexibility.

All parts and percentages in the examples which follow are by weight, unless otherwise indicated.

EXAMPLES

Amine 1 is Jeffamine T-3000

Amine 2—A round bottom flask was fitted with stirrer, heating mantle, nitrogen inlet, thermocouple and addition funnel. 1170 parts (1.0 equivalent) of Jeffamine T-3000 was added to the flask at room temperature. 125.13 parts (1.0 equivalent) N-ethylmalimide were then added. The temperature of the flask rose to 60° C. The reaction was then held at 60° C. for 24 hours at which time an iodometric titration showed that the reaction was complete. The reaction mixture was cooled to room temperature. The clear, nearly colorless final product has a viscosity of: 1420 cps and an amine number of 46.9: (theoretical amine number: 43.3).

Comparative Example—A round bottom flask was fitted with stirrer, heating mantle, nitrogen inlet, thermocouple and addition funnel. 500 parts (0.5 equivalents) of Jeffamine T-3000 was added to the flask at room temperature. 62.6 parts (0.5 equivalents) of diethyl maleate were then added. The temperature of the flask rose to 60° C. The reaction was then held at 60° C. for 24 hours at which time an iodometric titration shows that the reaction was only 24% complete. The reaction mixture was cooled and held at room temperature for two months at which time an iodometric titration showed the conversion to aspartate was only 50% complete.

The sample from Example 1 was hand mixed with Desmodur N-3300 (a trimerized hexane diisocyanate having an NCO content of 21.8% by weight and an equivalent weight of 192), indexed at a (NCO:NH)-ratio of 1. Viscosity was measured on a Brookfield Viscometer. Sample dry time was measured by doing a draw down of the mixed sample on glass. Samples were drawn down at 10 mils wet. At 2 minute intervals, a cotton ball was pressed on the draw down to test for film cure. The sample film is completely cured when the cotton ball doesn't leave an imprint. Shore D Hardness was measured by pouring the mixed sample into an aluminum cup and testing for hardness 3 days later with a Shore Durometer Type D-2, ASTM D2240.

| Product | Dry time (minutes) | Potlife | Shore D (3 days after mix) | Appearance of film |
|---|---|---|---|---|
| Example 1 | 25 | 10 | 13 | Clear |
| Amine 1 | — | <<10 second* | — | — |

*too fast to prepare test specimen

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A polyaspartimide of the formula:

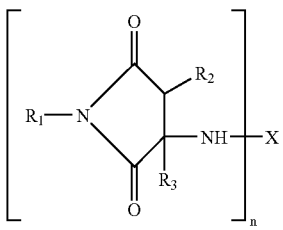

where

X represents an n-valent polyether radical obtained by the removal of n amino groups from a polyether amine corresponding to the formula, X—(NH$_2$)$_n$, wherein said polyether amine has a number average molecular weight of from about 200 to about 6000, and may contain further functional groups that either are reactive with isocyanate groups or are inert to isocyanate groups at temperatures of up to 100°C., R$_2$ and R$_3$ may be the same or different and represent moieties selected from the group consisting of i) hydrogen, ii) straight or branched C$_1$ to C$_8$ alkyl groups, which may be substituted with up to three aryl groups containing from 6 to 10 carbon atoms, iii) C$_6$ to C$_{10}$ aryl groups, which may be substituted with up to three alkyl groups having from 1 to 3 carbon atoms, and iv) together form a five or six-membered cycloalkyl group, with said cycloalkyl group being substituted with from 0 to 3 alkyl groups having from 1 to 3 carbon atoms, R$_1$ represents a moiety selected from the group consisting of i) hydrogen, ii) straight or branched C$_1$ to C$_8$ alkyl groups, which may be substituted with up to three aryl groups containing from 6 to 10 carbon atoms, and iii) C$_6$ to C$_{10}$ aryl groups, which may be substituted with up to three alkyl groups having from 1 to 3 carbon atoms, and n represents an integer of from 2 to 4.

2. A process for preparing a polyaspartimide of the formula:

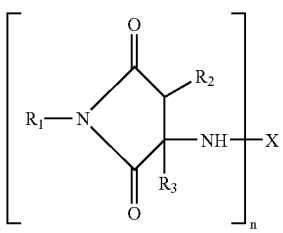

where

X represents an n-valent polyether radical obtained by the removal of a amino groups from a polyether amine corresponding to the formula, X-(NH$_2$)$_n$, wherein said polyether amine has a number average molecular weight of from about 200 to about 6000, and may contain further functional groups that either are reactive with isocyanate groups or are inert to isocyanate groups at temperatures of up to 100°C., R$_2$ and R$_3$ may be the same or different and represent moieties selected from the group consisting of i) hydrogen, ii) straight or branched C$_1$ to C$_8$ alkyl groups, which may be substituted with up to three aryl groups containing from 6 to 10 carbon atoms, iii) C$_6$ to C$_{10}$ aryl groups, which may be substituted with up to three alkyl groups having from 1 to 3 carbon atoms, and iv) together form a five or six-membered cycloalkyl group, with said cycloalkyl group being substituted with from 0 to 3 alkyl groups having from 1 to 3 carbon atoms, R$_1$ represents a moiety selected from the group consisting of i) hydrogen, ii) straight or branched C$_1$ to C$_8$ alkyl groups, which .may be substituted with up to three aryl groups containing from 6 to 10 carbon atoms, and iii) C$_6$ to C$_{10}$ aryl groups, which may be substituted with up to three alkyl groups having from 1 to 3 carbon atoms, and n represents an integer of from 2 to 4, comprising reacting at a temperature of from about room temperature to about 100°C., in solution or in the absence of a solvent, an amine of the formula

with a maleimide at a maleimide to amine group equivalent ratio is from about 0.95:1 to about 1.05:1, and wherein X and n are as defined above.

3. The process of claim 2, wherein said maleimide is of the formula:

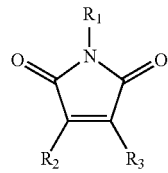

where R$_1$, R$_2$ and R$_3$ are as defined above.

4. The process of claim 2, wherein the maleimide to amine group equivalent ratio is 1:1.

5. A two-component coating composition which comprises, as binder,
   a) a polyisocyanate component and
   b) an isocyanate-reactive component containing
      b1) the polyaspartimide of claim 1,
      b2) optionally other isocyanate-reactive compounds,
wherein the equivalent ratio of isocyanate groups to isocyanate-reactive groups is from about 0.8:1 to about 2.0:1.

* * * * *